US006229072B1

(12) United States Patent
Burns et al.

(10) Patent No.: US 6,229,072 B1
(45) Date of Patent: May 8, 2001

(54) CYTOPLASMIC MALE STERILITY SYSTEM PRODUCTION CANOLA HYBRIDS

(75) Inventors: Dale R. Burns; Mark A. Forhan, both of Winnipeg (CA); Steve Barnes, Petit-Hallet (BE); Greg C. Buzza, Flagstone Creek (AU); Florin M. Stoenescu; Teresa Huskowska, both of Winnipeg (CA)

(73) Assignee: Adventa Technology Ltd, Sleaford (GB)

( * ) Notice: Subject to any disclaimer, the term of this patent is extended or adjusted under 35 U.S.C. 154(b) by 0 days.

(21) Appl. No.: 09/406,037

(22) Filed: Sep. 27, 1999

Related U.S. Application Data

(63) Continuation of application No. 08/675,156, filed on Jul. 3, 1996, now Pat. No. 5,973,233.

(30) Foreign Application Priority Data

Jul. 7, 1995 (GB) .................................................. 9513881

(51) Int. Cl.$^7$ .............................. A01H 5/00; A01H 5/10; A01H 1/00

(52) U.S. Cl. .......................... 800/306; 800/274; 800/298; 800/260; 47/58.1

(58) Field of Search .............................. 47/58.1; 800/267, 800/260, 266, 298, 306, 271, 274; 536/24.3

(56) References Cited

U.S. PATENT DOCUMENTS

| 4,658,084 | 4/1987 | Beversdorf et al. . |
| 5,356,799 | 10/1994 | Fabijanski et al. . |
| 5,478,369 | 12/1995 | Albertsen et al. . |
| 5,973,233 | * 10/1999 | Burns et al. .......................... 800/306 |

FOREIGN PATENT DOCUMENTS

| 652964 | 4/1992 | (AU) . |
| 599042 | 6/1994 | (EP) . |
| 671121 | 9/1995 | (EP) . |

OTHER PUBLICATIONS

Ecke et al. Bericht uber die Arbeitstagung der Arbeitsgemeinschaft der Saatzuchtleiter im Rahmen der Vereingung Osterreichsher Pflanzanzuchter, vol. 44, pp. 75–84 (translation pp. 1–28), 1993.*
Mailer et al. Canadian Journal of Plant Science, vol. 70, pp. 399–407, 1990.*
Visentin et al. Journal of Agricultural Food Chemistry, vol. 40, pp. 1687–1691, 1992.*
R. Delourme, A. Bouchereau, N. Hubert, M. Renard, B.S. Landry. Identification of RAPD Markers Linked to a Fertility Restorer Gene for Ogura Radish Cytoplasmic Male Sterility of Rapeseed (Brassica Napus L.). Theoretical Applied Genetics, vol. 88, pp. 741–748, 1994.
R. Pellan–Delourme and M. Renard. Cytoplasmic male sterility in rapeseed (Brassica Napus L.): female fertility of restored rapeseed with "Ogura" and cybrids cytoplasms. Genome, vol. 30, 1988.
F.W. Heyn. Transfer of Restorer Genes from Raphanus to Cytoplasmic Male Sterile Brassica napus and the Generics of Fertility Restoration. Cruciferase Newsletter 1:15–16, 1976.
R. Delourme, R. and F. Eber. Linkage Between and Isozyme marker and a restorer gene in a radish cytoplasmic male sterility of rapeseed (Brassica Napus L.). Theoretical and Applied Genetics vol. 85, pp222–228, 1992.
R. Mawson, R.K. Heany, Z. Zdunczyk and H. Kozlowska. Rapeseed meal–glucosinolates and their antinutritional effects. Part 5. Animal reproduction. Die Nahrung, 38 (1994) 6, 588–98.
R. Mawson, R.K. Heany, Z. Zdunczyk and H. Kozlowska. Rapeseed meal–glucosinolates and their antinutritional effects. Part 6. Taint in endproducts. Die Nahrung 39 (1995) 1, 21–31.
R. Mawson, R.K. Heany, Z. Zdunczyk and H. Kozlowska. Rapeseed meal–glucosinolates and their antinutritional effects. Part 1. Rapeseed production and chemistry of glucosinolates. Die Nahrung 37 (1993), 2, 131–140.
R. Mawson, R.K. Heany, Z. Zdunczyk and H. Kozlowska. Rapeseed meal–glucosinolates and their antinutritional effects. Part 3. Animal growth and performance. Die Nahring 38 (1994) 2, 167–177.
R. Mawson, R.K. Heany, Z. Zdunczyk and H. Kozlowska. Rapeseed meal–glucosinolates and their antinutritional effects. Part. 4. Goitrogenicity and internal organs abnormalities in animals. Die Nahrung 38 (1994) 2, 178–191.
F. Schöne, L, Leiterer, G. Jahreis and B. Rudolph. Effect of rapeseed feedstuffs with different glucosinolate content and iodine administration on gestating and lactating sow. J. Vet. Med. A. Augustus 1997; 44(6): 325–339.
R. Mawson, R.K. Heany, Z. Zdunczyk and H. Kozlowska. Rapeseed meal–glucosinolates and their antinutritional effects. Part. 7 Processing. Die Nahrung 39 (1995) 1, 32–41.
Y.K. Goh and D.R. Clandinin. Transfer of $^{125}$I to eggs in hens fed on diets containing high–and low glucosinolate rapeseed meals. Br. Poult Sci. 18 (1977): 705–710.

(List continued on next page.)

Primary Examiner—Gary Benzion
Assistant Examiner—Melissa L. Kimball
(74) Attorney, Agent, or Firm—Dana Rewoldt

(57) ABSTRACT

Our invention comprises a gene restorer line of *Brassica napus* which contains a *Raphanus sativus* restorer gene but is essentially free of *Raphanus sativus* genes which produce high glucosinolate. In particular, we provide a gene restorer line, and progeny derived therefrom, seed of which is low in glucosinolates. The *Brassica napus* restorer lines are free of glucosinolate-producing genes having a characteristic RFLP signature. The method of producing such lines which comprises crossing *Brassica napus* restorer lines and hybrids with desired *Brassica napus* germplasm and selecting progeny having a characteristic RFLP signature is also encompassed by the present invention.

21 Claims, 1 Drawing Sheet

OTHER PUBLICATIONS

G. Richter, A. Lemser and J. Bargholz, Rapssamen under Rapsextraktionsschrot als Komponenten in der Legehennenfütterung. Arch. Anim. Nutr., 1996, vol. 49, 229–241.

F. Schöne, G. Jahreis, R. Lange, W. Seffner, B. Groppel, A. Henning and H. Lüdke. Effect of varying glucosinolate and Iodine intake via rapeseed meal diets on serum thyroid hormone level and total iodine in the thyroid in growing pigs. Endocrinol Exp. vol. 24, 1990, pp 415–427.

F. Schöne, B. Rudolph, U. Kirchheim and G. Knapp. Counteracting the negative effects of rapeseed and rapeseed press cake in pig diets. Br. Journal of Nutr. (1997), 78, pp 947–962.

F.X. Aherne, A.J. Lewis. The nutritive value of faba beans and low glucosinolate rapeseed meal for swine. Adv. Exp. Med. Biol. 1978, 105, pp 453–471.

T.K. Smith and L.D. Campbell. Rapeseed meal glucosinolates: Metabolism and effect on performance in laying hens. Poult. Sci. (1976) 55: pp 861–867.

P. Kloss, E. Jeffery, M. Wallig, M. Tumbleson and C. Parsons. Efficacy of feeding glucosinolate–extracted crambe meal to broiler chicks. Poult Sci. (1994) 73: 1542–1551.

M. Vermorel, M.J. Davicco and J. Evrard. Valorization of rapeseed meal. 3. Effects of glucosinolate content of food intake, weight gain, live weight and plasma thyroid hormone levels in growing rats. Reprod. Nutr. Develop. (1987), 27, (1A), pp 57–66.

G.P. Lardy, and M.S. Kerley. Effect of increasing the dietary level of rapeseed meal on intake by growing beef steers. J. Anim. Sci. (1994), 72: 1936–1942.

P.A.L. Weight, R.K. Scougall, D.W.F. Shannon and J.W. Wells. Role of glucosinolates in the causation of liver haemorrhages in laying hens fed water–extracted or heat–treated rapeseed cakes. Res. Vet. Sci. (1987) 43, pp 313–319.

R. Magrath, C. Herron, A. Giamoustaris and R. Mithen. The inheritance of aliphatic glucosinolates in Brassica napus. Plant Breeding 111: 55–72.

D.I. McGregor and R.K. Downey. A rapid and simple assay for indentifying low glucosinolate rapeseed. Can J. Plant Sci. 55: 191–196, Jan. 1995.

B. Rücker and G. Röbbelen. Inheritance of total and individual glucosinolate content in seeds of winter oilseed rape (Brassica napus L.). Plant Breeding 113: 206–216, 1994.

D. Toroser, C.E. Thormann, T.C. Osborn and R. Mithen. RFLP mapping quantitative trait loci controlling seed alophatic glucosinolate content in oilseed rape (Brassica napus L.). Theor Appl. Genet (1995) 91:802–808.

* cited by examiner

CYTOPLASMIC MALE STERILITY SYSTEM PRODUCTION CANOLA HYBRIDS

This application is entitled to the benefits of foreign priority under Title 35 U.S.C. section 119. The foreign priority document is United Kingdom application 9513881.4 filed on Jul. 7, 1995. This application is a continuation application filed on Sep. 27, 1999 and is entitled to the benefits of the filing date of the earlier filed copending application entitled Cytoplasmic Male Sterility system producing Canola Hybrids, U.S. Ser. No. 08/675,156 filed on Jul. 3, 1996 which is entitled to the benefit of foreign priority under title 35 USC 119 based on U.K. application 9513881.4 filed on Jul. 7, 1995. The U.S. application issued into U.S. Pat. No. 5,973,233.

FIELD OF THE INVENTION

This invention relates to improved plants. In particular, it relates to new plant germplasm of the Brassica species, having a reduced content of undesired glucosinolates.

BACKGROUND OF THE INVENTION

Economic production of Brassica spp. hybrids requires a pollination control system and effective transfer of pollen from one parent to the other. The ogura cytoplasmic male sterility (cms) system, developed via protoplast fusion between radish (*Raphanus sativus*) and rapeseed (*Brassica napus*) is one of the most promising methods of hybrid production. It provides stable expression of the male sterility trait (Ogura 1968), Pelletier et al. (1983) and an effective nuclear restorer gene (Heyn 1976).

Initial restorer material showed reduced female fertility which was overcome through backcrossing. Delourme et al. (1991) attributed this to elimination of a portion of the radish chromosome that had been introduced along with the restorer gene. In their work, successive backcross generations produced fertility levels successively closer to normal.

High glucosinolate (GSL) content in seed of *Brassica napus* is an anti-nutritional factor. Meal made from such seed is unsuitable for use in animal feeds. Seed GSL level is an expression of the genotype of the female plant and is determined by four to eight separate dominant and additive genes. Two to five genes are involved in alkenyl (one of the aliphatic group) glucosinolate content, while two or three genes are involved in indole glucosinolate content (Rücker and Röbbelen, 1994). Total aliphatics may be determined by up to six genes (Magrath et al. 1993).

SUMMARY OF THE INVENTION

An object of the present invention is to provide Brassica spp. hybrids, seeds, microspores, ovules, pollen, vegetative parts containing low glucosinolate and the restorer gene.

Yet another object of the present invention is to provide interspecific crosses using fertile, low glucosinolate plants with the ogura cytoplasm as the female, followed by selection for fertility and low glucosinolate.

A further object of the invention is to provide a method for identifying a restorer line that contains only the portion of the *Raphanus sativus* material necessary for fertility and not the portion of the *Raphanus sativus* material that produces high glucosinolate.

Accordingly, our invention comprises a gene restorer line of *Brassica napus* which contains a *Raphanus sativus* restorer gene but is essentially free of *Raphanus sativus* glucosinolate-producing genes. In particular, we provide the gene restorer line KH, and progeny derived therefrom, seed of which is low in glucosinolates. We further provide *Brassica napus* restorer lines free of glucosinolate-producing genes having a characteristic RFLP signature, as hereinafter described, and a method of producing such lines which comprises crossing *Brassica napus* restorer and/or hybrid lines with desired *Brassica napus* germplasm and selecting progeny having a characteristic RFLP signature. Clearly this invention encompasses hybrids containing the restorer gene without the high glucosinolate material. Additionally, these hybrids can be used to create new restorer lines within the scope of this invention.

The present invention broadly includes a method of producing an improved restorer line of Brassica for use in a cytoplasmic male sterility system, which comprises forming a plant population from a gene restorer line of *Brassica napus* which contains a *Raphanus sativus* restorer gene and *Raphanus sativus* glucosinolate genes. Then breeding with the progeny of the plant population. Furthermore, it includes testing the progeny for fertility indicating the *Raphanus sativus* restorer gene is present and for levels of glucosinolate wherein the presence and absence of *Raphanus sativus* high glucosinolate production is shown; and selecting progeny which are positive for presence of the restorer gene and negative for the *Raphanus sativus* with glucosinolate production.

The inventive methods of this application also include a method of forming *Brassica napus* hybrid seed and progeny thereof from a cytoplasmic male sterility system which includes a restorer line containing *Raphanus sativus* restorer gene. This method includes the steps of providing a homozygous improved restorer line produced, as outlined above, using the restorer line in a hybrid production field as the pollinator; using cytoplasmic male sterile plants in a hybrid production field as the hybrid seed producing plant; and harvesting the hybrid seed from the male sterile plant.

Additionally, when producing progeny, the method includes the step of planting the hybrid seed from the male sterile plant and growing a plant therefrom.

The present invention clearly shows how to form an improved Brassica ssp., an improved *Brassica napus* plant, having low glucosinolate seeds, the plant containing *Raphanus sativus* gene material that is capable of restoring fertility to the ogura cytoplasmic male sterile plants, the improvement comprising an improved *Brassica napus* plant evidencing deficient glucosinolate production from the *Raphanus sativus* material, wherein the improved plant produced low glucosinolate seeds.

A *Brassica napus* plant containing *Raphanus sativus* restorer gene unlinked from *Raphanus sativus* glucosinolate genes adapted to restore fertility to oguracytoplasmic male sterile.

The present invention describes the molecular marker method. This is a method wherein the markers mapping to similar regions as those in the group consisting of, WG3F7, TG1H12, OPC2, WG4D10, WG6F3 are employed to identify the *Raphanus sativus* material which contains high glucosinolate producing genes.

The present invention encompasses not only canola quality but any low glucosinolate material produced for a cytoplasmic sterile plant containing *Raphanus sativus*. Any canola quality (erucic acid<2% and <30 μmoles glucosinolates/gram defatted dry meal) restorer line, capable of inducing fertility in Brassica plants containing the INRA Ogura cytoplasmic male sterility. Further, the present invention encompasses Brassica spp. hybrids, seeds, microspores, ovules, pollen, vegetative parts containing low glucosinolate restorer gene. Interspecific crosses using fertile, low glucosinolate plants with the ogura cytoplasm as the female, followed by selection for fertility and low glucosinolate.

Brassica spp. hybrids, seeds, microspores, ovules, pollen, vegetative parts containing low glucosinolate restorer gene as identified by using probes such as those as described herein.

Additionally in the broad scope of the invention included is the *Brassica napus* (spring and winter types) or *B. rapa* containing the low glucosinolate restorer gene as described.

DETAILED DESCRIPTION OF INVENTION

Figure 1:
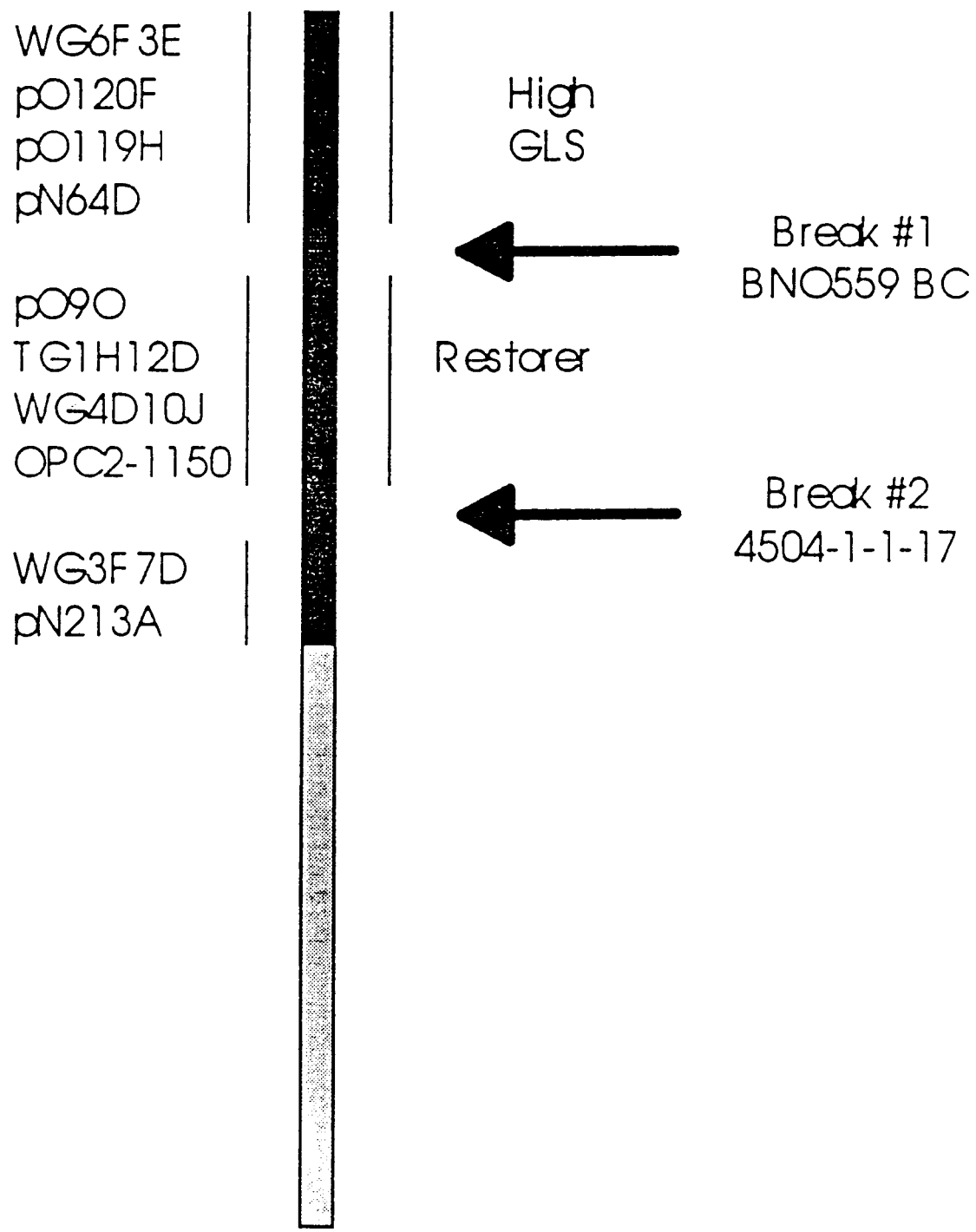
FIG. 1 is a schematic map showing the relation of high GSL genes to the restorer gene in ogura germplasm, as revealed by our work, and the location of probes binding in this area.

We now describe genes for high seed glucosinolate content (GSL) which were also introduced with the restorer gene. In addition, we describe our work which has broken the very tight linkage between the radish-derived restorer gene and the non-canola quality levels of glucosinolates in the seed. The resulting lines are the first canola quality restorers for this cms system, which in turn produce the first fully fertile ogura cms canola hybrids. The terms hybrid, line and plant or progeny when used in the claims includes but are not limited to seeds, microspores, protoplasts, cells, ovulas, pollen, vegetative parts, cotyledons, zygotes and the like.

Background

The original *Brassica napus* restorer material, RF, used in our work, is an F6 line from the cross
FU58.Darmor BC1/Rest.Darmor BC1//Bienvenu,
and was obtained from the Institut National de Recherches Agricoles (INRA) in 1992. This material is commercially available under license from INRA. This material is biennial, low erucic acid (C22:1) and high GSL. It therefore required backcrossing into elite spring types for use in our spring hybrid program.

All fertile F1 plants from RF crossed by spring lines tested high for aliphatic glucosinolate as expected. However, corresponding steriles possessed GSL levels of less than 30 μmoles/gram defatted dry meal. This indicated an extremely tight linkage between the restorer and high GSL genes. Absence of high GSL sterile plants also indicated the lack of high GSL genes normally found in rapeseed. Except for the presence of the radish GSL genes, fertile plants should therefore have been canola quality. High GSL content in seed of fertile plants therefore was derived from radish DNA inserted with the restorer gene.

Based on the theory of a single dominant gene for fertility restoration and another single dominant gene complex for GSL content, individual plants were expected to segregate as follows in subsequent backcross generations:

½ male sterile
¼ high GSL, fertile
¼ low GSL, fertile

Of 493 BC1 crosses studied, no low GSL fertile plants were obtained. Over 298 BC2 crosses also failed to produce low GSL restorers. This again points to a very strong linkage between the restorer gene and the radish-derived high GSL genes. Restored plants possessed elevated levels of progoitrin and gluconapin compared to control plants. Levels of sinapine, glucoalysin and glucobrassicanapin fluctuated in the restored plants relative to controls (Table 1).

Delourme et al. (1994), using RAPD markers, concluded that radish DNA had been retained around the restorer gene. Our RFLP data showed that the portion of the Raphanus chromosome which was introgressed into the Brassica genome contained the radish high GSL genes in addition to the restorer.

The absence of low GSL restorers was observed as far as the BC7 generation in the 1994 Zeneca Seeds nursery in Carman, Manitoba. Over 700 backcrosses (BC1 to BC6) were performed in the 1994 field program using emasculated fertile plants containing the ogura cytoplasm (therefore containing the restorer gene) as the female. In addition, over 500 doubled haploids from various restorer by germplasm crosses were evaluated. All doubled haploids were high (over 30 μmoles/gram) GSL.

Of the 700 backcrosses, three gave rise to seed which was found to have low (<30 μmoles/gram dry seed) GSL levels, equal to sterile plants in the row. All three (KH-A, KH-B, KH-C) were BC2 progeny of the proprietary Zeneca Seeds line BNO559 originally crossed to a restorer gene source KH in November 1993. The restorer gene source KH for the line was a BC1 plant of the original restorer source from INRA (RF) crossed twice to a Zeneca Seeds inbred 4372 (RF<2<4372). Review of the history of the line KH (RF<2<4372)<2<BNO559 indicated a prior generation of low GSL results in the controlled environment growth room.

TABLE 1

Comparison of Glucosinolate Profiles of High GSL Restored Plants in ogura Cytoplasm and Corresponding Fertile Parent in Normal Cytoplasm*.

| # | Pedigree | PRO | EPI | SIN | NAP | ALY | GNA | 4OH | GBN | GBC | NAS | NEO | ALI | IND | TOT |
|---|---|---|---|---|---|---|---|---|---|---|---|---|---|---|---|
| 1 | RF<5<BN0027-22-1-1 | 11.31 | 0.36 | 1.26 | 0.18 | 0.19 | 3.13 | 2.56 | 0.22 | 0.21 | 0.29 | 0.02 | 16.64 | 3.08 | 19.72 |
| 2 | RF<5<BN0027-22-1-2 | 32.13 | 0.84 | 6.42 | 0.44 | 1.73 | 7.75 | 3.09 | 0.72 | 0.19 | 0.91 | 0.06 | 49.83 | 4.26 | 54.09 |

TABLE 1-continued

Comparison of Glucosinolate Profiles of High GSL Restored Plants in ogura
Cytoplasm and Corresponding Fertile Parent in Normal Cytoplasm*.

| # | Pedigree | PRO | EPI | SIN | NAP | ALY | GNA | 4OH | GBN | GBC | NAS | NEO | ALI | IND | TOT |
|---|---|---|---|---|---|---|---|---|---|---|---|---|---|---|---|
| 7 | RF<4<BN0027-22-1-2 | 30.89 | 0.60 | 7.23 | 0.26 | 0.94 | 8.94 | 2.09 | 0.30 | 0.42 | 2.96 | 0.01 | 49.16 | 5.49 | 54.64 |
| 8 | RF<S<BN0027-22-1-2 | 29.77 | 0.58 | 5.08 | 0.28 | 0.93 | 7.58 | 1.96 | 0.48 | 0.50 | 1.82 | 0.01 | 44.70 | 4.29 | 48.99 |
| 13 | RF<5<BN0027-22-1-3 | 22.74 | 0.45 | 2.80 | 0.16 | 1.16 | 8.26 | 2.04 | 0.88 | 0.27 | 2.33 | 0.02 | 36.45 | 4.65 | 41.10 |
| 14 | RF<5<BN0027-22-1-3 | 22.37 | 0.44 | 3.19 | 0.18 | 0.61 | 5.01 | 1.77 | 0.23 | 0.35 | 1.53 | 0.02 | 32.04 | 3.87 | 35.72 |
| 15 | BN0027-22-1-1 | 2.27 | 0.04 | 1.47 | 0.12 | 0.06 | 0.60 | 1.52 | 0.23 | 0.32 | 1.64 | 0.03 | 4.80 | 3.51 | 8.31 |
| 16 | BN0027-22-1-2 | 1.79 | 0.04 | 1.28 | 0.11 | 0.05 | 0.49 | 1.50 | 0.02 | 0.16 | 1.97 | 0.05 | 3.78 | 3.68 | 7.47 |
| 17 | BN0027-22-1-3 | 1.12 | 0.02 | 0.00 | 0.10 | 0.03 | 0.34 | 1.20 | 0.20 | 0.09 | 0.98 | 0.02 | 1.82 | 2.29 | 4.10 |

Legend for Table 1

| ALIPHATIC GLUCOSINOLATE | Code | INDOLE GLUCOSINOLATE | Code | MISC. | Code |
|---|---|---|---|---|---|
| Progoitrin | PRO | 4-Hydroxy Glucobrassicin | 4OH | Total alipha-tics | ALI |
| Epiprogoitrin | EPI | Glucobrassicin | GBC | | |
| Sinigrin | SIN | Gluconasturtiin | NAS | Total indoles | IND |
| Napolederin | NAP | Neoglucobrassicin | NEO | | |
| Glucoalysin | ALY | | | Total GSL | TOT |
| Gluconapin | GNA | | | | |
| Glucobrassicanapin | GBN | | | | |

* Results obtained using HPLC analysis for glucosinolate profile. This is the standard protocol well known to those of skill in the art.

To verify that KH was in fact a low GSL restorer (R) line, a three-step approach was used.

1) GSL levels of subsequent generations were again evaluated in the field,

2) Genetic studies were conducted to verify inheritance of the restorer gene and 3) RFLP analyses were used to determine differences between high GSL and canola-quality lines or low GSL lines and plants.

1) Verification of Glucosinolate Levels

Material was grown in the nursery (November 94-March 95) in Tasmania, Australia for glucosinolate evaluation of a third generation. The three low GSL BC2 lines KH-A, -B, -C, were planted in three separate rows, along with high GSL sister lines (different original cross to BNO559) and non-related restorers in adjacent plots. Since expression of GSL content in the seed is not affected by pollen source (Magrath et el. 1993), both selfed and open-pollinated seed was tested from these rows. As shown in Table 3, only plants descended from KH, the original RF<3<BNO559-3-2, were again low GSL. Sister lines also derived from BNO559 were not. Thus it appears that the break in the linkage between the restorer gene and the adjacent high GSL genes occurred as the result of a specific meiotic event which was "captured" in one cross (Table 2). All radish-derived GSL genes were lost in the one event; therefore, they had been tightly linked together as a complex acting like a single dominant gene linked to the restorer gene.

TABLE 2

| Source | Gluc(9)* |
|---|---|
| RF < 3 < (BNO559)-1-2-1)-1 | 5.4 |
| RF < 3 < (BNO559)-1-2-1)-2 | 4.5 |
| RF < 3 < (BNO559)-2-2-2)-1 | 5.5 |
| RF < 3 < (BNO559)-2-2-2)-2 | 6.6 |
| RF < 3 < (BNO559)-2-4-1)-1 | 4.4 |
| RF < 3 < (BNO559)-2-4-1)-2 | 5.4 |
| RF < 3 < (BNO559)-3-1-1)-1 | 4.4 |
| RF < 3 < (BNO559)-3-1-1)-2 | 4.4 |
| RF < 3 < (BNO559)-3-2-1)-1 | 2.2 |
| RF < 3 < (BNO559)-3-2-1)-2 | 3.2 |
| RF < 3 < (BNO559)-3-2-2)-1 | 2.2 |
| RF < 3 < (BNO559)-3-2-2)-2 | 2.2 |
| RF < 3 < (BNO559)-3-2-2)-3 | 2.3 |
| RF < 3 < (BNO559)-3-2-3)-1 | 3.2 |
| RF < 3 < (BNO559)-3-2-3)-2 | 2.3 |
| RF < 3 < (BNO559)-4-3-2)-1 | 4.5 |
| RF < 3 < (BNO559)-4-3-2)-2 | 3.4 |

Table 2—shows glucosinolate results from Tasmania nursery 1994–95. Bolded cells indicate progeny of low GSL row in 1994 Carman nursery. (GSL ratings 1–9 using Tes-Tape method, where canola quality <3. *Duplicate analyses performed on each sample).

There are at least two well known methods of testing for glucosinolate. The first test is for quantitative glucosinolate analysis using high performance liquid chromatography. This test is cited in ISO Method 9167-1:1992. Rapeseed— Determination of glucosinolates content—Part 1: Method using high-performance liquid chromatography, International Organization for Standardization, Geneva.

The second test is described below:

The Tes-Tape Method for Evaluation of Seed Glucosinolate Content in Brassicas. (Based on Rakow et al. (1981).

1. Place 5 seeds in a microtitre plate well.
2. Crush seed using a rod and light hammer stroke, cleaning rod between samples.
3. Add 100 $\mu$L (microliters) of distilled water or 100 $\mu$L or 1 millimolar sodium ascorbate if seed is old (reduced viability).
4. Wait 10 minutes.
5. Add 25 $\mu$L of 70 g/L charcoal solution.
6. Wait 1 minutes.
7. Insert a 2 cm strip of Tes-Tape (normally used to test for glucose content in urine of diabetics).
8. Wait 5 minutes.
9. Read Tes-Tape color change. Color change may be based on either a 1–5 or 1–9 scale as follows:

```
| 1 |   | 2 |   | 3 |   | 4 |   | 5 |
| 1 | 2 | 3 | 4 | 5 | 6 | 7 | 8 | 9 |
```
         ↑              ↑
  15 μmoles/gram  30 μmoles/gram
                (Canola Standard)

The low GSL trait was expressed for a third consecutive generation in progeny of the RF<2<BNO559-3-2 line (bolded rows). All plants harvested from the line were canola-quality. Sister lines and non-related strains (data not shown) were all high (rapeseed levels). Using a Wilcoxon Rank Test, with normal approximation and a continuity correction of 0.5, the GSL values of the identified line were significantly lower than closely related sister lines (p=0.0001). Statistically, this line is significantly lower in glucosinolates than any other ogura restorer.

2) Verification of Restorer Gene Using Genetic Studies 2.a) Testcrosses

The putative restorer line KH, RF<3<BNO559-3-2, was crossed to five genetically-diverse male-sterile lines possessing the ogura cytoplasm. Since the restorer gene was first identified in a backcross-derived line, F1 plants derived from these crosses were expected to segregate evenly for fertiles and steriles. As shown in Tables 3 and 4A, testcross progeny data support the concept of a single dominant gene for restoration.

TABLE 3

| Female | # Steriles | # Fertiles |
| --- | --- | --- |
| 1 | 36 | 34 |
| 2 | 50 | 43 |
| 3 | 78 | 63 |
| 4 | 71 | 67 |
| 5 | 76 | 73 |
| Observed Total | 311 | 280 |
| Expected Total | 295.5 | 295.5 |

Table 3—testcross results using BC2F1 plants as restorer gene source.

The Chi-Square value calculated for Goodness of Fit of these results to the expected 1:1 ratio is 1.626 with 1 degree of freedom (p=0.20). The results are therefore not statistically distinguishable from those expected (Steele and Torrie, 1980).

2.b) F2 Segregation Ratios

BC2 plants were also selfed in order to determine segregation ratios of the BC2F2 population. Six hundred and eighty-six single F2 plants were evaluated for fertility status. Based on the assumption of a single dominant gene originally introduced from the radish parent, the F2 population should have segregated 3 Fertile: 1 Sterile. As shown in Table 5, observed results were close to expected values.

TABLE 4A

| Class | Fertile | Sterile |
| --- | --- | --- |
| Number of plants observed | 499 | 187 |
| Theoretical number of plants expected | 514.5 | 171.5 |

Table 4A —Frequency distribution of F2 population.

The Chi-Square value for Goodness of Fit calculated for these results is 1.868 with 1 degree of freedom (p=0.17). The results are therefore not statistically different from expected values (Steele and Torrie, 1980).

Examples Of Using Hybrid As Source Of Restorer Gene

Selfing Down Of Hybrid

Low glucosinolate hybrids containing the new restorer gene were grown out. Fertile plants were self pollinated, some with bags, others by brushing pollen manually. F2 seed was harvested from these F1 plants and planted as a population. Fertile plants from the population were selected and grown as F3 rows, thereby providing starting material for breeding approaches such as pedigree breeding, recurrent selection and others.

As Parent In Traditional Breeding

Lines containing the improved restorer gene were crossed with other germplasm lines as part of the breeding program. The F1 from these crosses was grown out. Fertile plants were self pollinated and resultant F2 seed harvested. Fertile plants from the F2 population were selected, harvested and grown as F3 rows, thereby providing starting material for breeding approaches such as pedigree breeding, recurrent selection and others.

As Parent In Doubled Haploid

A source of the improved restorer gene was crossed to improved germplasm. The resulting hybrids, 94-0186 and 94-0187, underwent microspore culture to produce doubled haploid restorer lines. Microspore culture methods utilized were similar to those described by Chen et al (1994) and Mollers et al (1994). These restorer lines have been verified as low glucosinolate.

As A Source Of Restorer In Backcross Program

Material containing the improved restorer gene was crossed to selected Zeneca Seeds' inbred lines. Fertile plants were emasculated and crossed again to the inbred line (recurrent parent). Resulting fertiles were backcrossed again to the inbred line. At any generation, selfing down of material could begin to produce new restorer lines. These projects exemplify a backcrossing program to bring the restorer gene into superior germplasm. The RFLP analysis could be employed to assist in early selection of plants having a favorably marker signature for low glucosinolate production in combination with having the restorer gene.

Field Segregation

F3 rows from BN0611 were planted in the nursery. The expected segregation ratio was 2:1 (segregating rows: fully fertile rows). Some rows exhibited very poor emergence with most of these containing only fertile plants. Unexpectedly, the segregation results were 340 segregating to 105 fertile, far from the 2:1 ratio expected from a single gene inheritance.

Doubled Haploids

The original BN0611 (a BC2 line) underwent microspore culture to produce true-breeding restorer lines. Again, unexpectedly, of the plants which successfully underwent chromosome doubling, the proportion of fertiles was vastly less than expected. The frequency was 254 steriles: 106 fertiles instead of a 1:1 ratio. These results, combined with field results, may indicate that low glucosinolate restoration is controlled by more than a single dominant gene or that the *Raphanus sativus* material is not well integrated into the genome. Additional theories may ultimately give other reasons for this unexpected segregation ratio.

Testcrosses

Twenty BN0611 F3 rows were chosen for being homozygous for the restorer gene. A single plant from each row was crossed to a male sterile line. F1 seeds were planted from each testcross and allowed to flower, at which time fertility of the F1 plants were evaluated.

| Cross | Male | Steriles | Fertiles | Haploids |
|---|---|---|---|---|
| 0089 | BN0611-1)-2-2}:11 | 0 | 6 | 0 |
| 0090 | BN0611-1)-2-4}:11 | 0 | 24 | 0 |
| 0091 | BN0611-1)-3-4}:11 | 0 | 19 | 0 |
| 0092 | BN0611-1)-8-2}:11 | 0 | 13 | 0 |
| 0093 | BN0611-1)-10-3}:11 | 0 | 27 | 0 |
| 0094 | BN0611-1)-16-2} | 0 | 24 | 0 |
| 0095 | BN0611-1)-22-1}:11 | 0 | 26 | 1 |
| 0096 | BN0611-1)-22-3}:11 | 0 | 15 | 1 |
| 0097 | BN0611-1)-22-4} | 0 | 24 | 0 |
| 0098 | BN0611-1)-22-5}:11 | 0 | 26 | 0 |
| 0099 | BN0611-1)-28-3}:11 | 0 | 22 | 1 |
| 0100 | BN0611-1)-31-1}:11 | 0 | 6 | 1 |
| 0101 | BN0611-1)-31-4}:11 | 0 | 17 | 1 |
| 0102 | BN0611-2)-7-2}:11 | 0 | 25 | 2 |
| 0103 | BN0611-2)-7-3}:11 | 14 | 9 | 1 |
| 0104 | BN0611-2)-7-6}:11 | 15 | 11 | 0 |
| 0105 | BN0611-2)-8-5}:11 | 0 | 5 | 0 |
| 0106 | BN0611-2)-9-5}:11 | 0 | 21 | 1 |
| 0107 | BN0611-2)-11-4}:11 | 0 | 21 | 0 |

Many F3 lines included a plant which had traits associated with haploids, i.e. very small buds and flowers. These plants also appeared to have a different leaf type than the other F1's, having a deeper lobed leaf. It may be possible that these plants are aneuploids, and that the extra genetic material could be causing the observed difference in leaf morphology.

New F3 Lines

The three low glucosinolate lines crossed by B line have been tested for segregation ratio of the F2 and F3 plants. Table 4B shows results again distinctly different from expected ratios.

TABLE 4B

| Cross | F2 Fertile | F2 Sterile | F3 Segregating | F3 Fertile |
|---|---|---|---|---|
| 0181 | n/a | n/a | 140 (110) | 25 (55) |
| 0184 | 67 (81) | 41 (27) | 57 (43) | 07 (21) |
| 0189 | 119 (118) | 38 (39) | 146 (116) | 28 (58) |

These results are far from the expected ratio of two segregating F3 lines for every homozygous line. There is frequently a bias toward fewer fertiles than would be expected from a single gene as the gene approaches homozygosity.

Glucosinolate Data

Quantitative glucosinolate data on a number of the lines are included in the following Table 4C.

TABLE 4C

| Pedigree | PRO | EPI | SIN | NAP | ALY | GNA | 40H | GBN | GBC | NAS | NEO | ALI | IND | TOT |
|---|---|---|---|---|---|---|---|---|---|---|---|---|---|---|
| RF<5<BN0027-22-1-1 | 11.31 | 0.36 | 1.26 | 0.18 | 0.19 | 3.13 | 2.56 | 0.22 | 0.21 | 0.29 | 0.02 | 16.64 | 3.08 | 19.72 |
| RF<5<BN0027-22-1-2 | 32.13 | 0.64 | 6.42 | 0.44 | 1.73 | 7.75 | 3.09 | 0.72 | 0.19 | 0.91 | 0.06 | 49.83 | 4.26 | 54.09 |
| RF<4<BN0027-22-1-2 | 30.89 | 0.60 | 7.23 | 0.26 | 0.94 | 8.94 | 2.09 | 0.30 | 0.42 | 2.96 | 0.01 | 49.16 | 5.49 | 54.64 |
| RF<5<BN0027-22-1-2 | 29.77 | 0.58 | 5.08 | 0.28 | 0.93 | 7.58 | 1.96 | 0.48 | 0.50 | 1.82 | 0.01 | 44.70 | 4.29 | 48.99 |
| RF<5<BN0027-22-1-3 | 22.74 | 0.45 | 2.80 | 0.16 | 1.16 | 8.28 | 2.04 | 0.88 | 0.27 | 2.33 | 0.02 | 36.45 | 4.65 | 41.10 |
| RF<5<BN0027-22-1-3 | 22.37 | 0.44 | 3.19 | 0.18 | 0.61 | 5.01 | 1.77 | 0.23 | 0.35 | 1.53 | 0.02 | 32.04 | 3.87 | 35.72 |
| BN0027-22-1-1 | 2.27 | 0.04 | 1.47 | 0.12 | 0.06 | 0.60 | 1.52 | 0.23 | 0.32 | 1.64 | 0.03 | 4.80 | 3.51 | 8.31 |
| BN0027-22-1-2 | 1.79 | 0.04 | 1.28 | 0.11 | 0.05 | 0.49 | 1.50 | 0.02 | 0.16 | 1.97 | 0.05 | 3.78 | 3.88 | 7.47 |
| BN0027-22-1-3 | 1.12 | 0.20 | 0.00 | 0.10 | 0.03 | 0.34 | 1.20 | 0.20 | 0.09 | 0.98 | 0.02 | 1.82 | 2.29 | 4.10 |
| RF<3<(BN0559)-3-2-1]-8-2 | 4.39 | | | 0.01 | 0.12 | 1.70 | 6.77 | 2.79 | 0.01 | 0.32 | 0.02 | 9.79 | 7.19 | 16.98 |
| RF<3<(BN0559)-3-2-2)-16-5 | 4.82 | | | 0.01 | 0.11 | 1.41 | 3.91 | 2.41 | 0.10 | 0.24 | 0.02 | 9.45 | 4.32 | 13.77 |
| RF<3<(BN0559)-3-2-3]-27-2 | 2.85 | | | 0.01 | 0.08 | 1.54 | 4.07 | 1.26 | 0.08 | 0.08 | 0.01 | 6.12 | 4.37 | 10.49 |
| BN0111+BN0018 check | 1.85 | | | 0.01 | 0.06 | 0.95 | 4.15 | 2.40 | 0.09 | 0.08 | 0.03 | 5.62 | 4.50 | 10.12 |

-continued

| Cross | Male | Steriles | Fertiles | Haploids |
|---|---|---|---|---|
| 0108 | BN0611-2)-11-5}:11 | 0 | 26 | 0 |

The fertile plants did exhibit some abnormal characteristics such as missing petals, malformed buds and bent stigmas. The severity of these traits varied by cross, suggesting some genetic influence by the male.

Crosses 103 and 104 shows a 1:1 segregation. Emergence data from the field showed that these two males had very few plants in the row, and thus had been mis-classified "homozygous".

The second group of data (on the previous page) comes from the Carman, Manitoba breeding nursery. As expected, there are some changes in levels of individual glucosinolates due to environmental factors (Mailer and Cornish, 1987). However, it is clear that the level of progoitrin (2-Hydroxy-4-pentenylglucosinolate) and gluconapine are significantly lower in the RF<3<(BN0559)-3-2 derived lines than in high glucosinolate material with the original restorer gene obtained from INRA.

3) RFLP Results 3.a) Mapping Of The Restorer Gene Locus

In order to determine the position of the restorer gene on the *Brassica napus* genetic map, DNA was purified from members of a BC1 population that was segregating for the presence of the restorer gene (scored as male fertility in a sterile cytoplasm). The DNA samples were digested with restriction endonucleases, subjected to agarose gel electrophoresis, and transferred to nylon membranes (essentially as described by Southern, 1975). The membranes were then treated with heat-denatured, $^{32}$P-labeled DNA probes (Sharpe et al, Osborn et al) and, following overnight hybridization and washing at an appropriate stringency, subjected to autoradiography. The RFLP patterns revealed by these probes were noted, and the probes giving bands of hybridization showing linkage to the restorer phenotype are shown in Table 5. A number of characteristic ("diagnostic") alleles were seen at the RFLP loci linked to the restorer locus, that are not present in the majority of canola germplasm. In addition to the RFLP probes, one oligonucleotide primer was used to generate RAPD patterns, recently published as being linked to the Restorer gene (Landry et al., 1994); this is also shown in Table 5. The use of AFLP, RFLP, RAPD, microsatellites, primer and other probes, etc. to give genetic fingerprints of the *Raphanus sativus* material and surrounding Brassica material is encompassed within the scope of this invention.

3.b) Characterization Of Low GSL Fertile Recombinants

Representative samples from the backcrosses that generated low GSL recombinants, described in sections 1 and 2, above, were analyzed with the probes listed in Table 5. The tight linkage between the restorer gene and the diagnostic RFLP alleles was maintained in the wide range of crosses being studied. Two recombination events are shown. The diagnostic alleles "lost" in these plants permit their loci to be placed in a slightly random order along the chromosome, relative to the restorer locus (illustrated in FIG. 1). Two separate recombination events have occurred—one in family BNO599, in which the high GSL region has been separated from the restorer, and a second in family 4504, where the restorer region has also been lost.

The GSL levels of the various plants are shown alongside the genotypes in Table 6. (GLS levels were measured by the HPLC method for evaluation of seed glucosinolate content in Brassicas. This indicates that the gene encoding high GSL levels is linked to the diagnostic alleles, and lies on the segment of chromosome marked by pO120, pO119 and pN64. Because of the low frequency of recombination in this region of the genome, it is impossible to quote precise distances. However, it is clear that by selecting fertile plants that lack the diagnostic alleles for the linked loci, it should be possible to improve the frequency of low GSL fertile plants in the backcross progeny.

TABLE 6

| Segregating plant | pN213A | WG3F7D | TG1H12D | OPC2 1150 | WG4D10J | pO9O | Fertility | pN64D | pO119H | pO120F | WG6F3E | Glucosinolates | GSL (2 reps) |
|---|---|---|---|---|---|---|---|---|---|---|---|---|---|
| FR2<2<4504-1-1/4504-1-1 pl 6 | + | + | + | + | + | + | F | + | + | + | + | H | 67.5, 68.1 |
| FR2<2<4504-1-1/4504-1-1 pl 12 | − | − | − | − | ? | − | S | − | − | − | − | L | 8.3, 10.9 |
| FR2<2<4504-1-1/4504-1-1 pl 5 | + | + | + | + | + | + | F | + | + | + | + | H | 69.9, 69.6 |
| FR2<2<4504-1-1/4504-1-1 pl 6 | + | + | + | + | + | + | F | + | + | + | + | H | 67.5, 68.01 |
| FR2<2<4504-1-1/4504-1-1 pl 17 | + | + | − | − | ? | − | S | − | − | − | − | L | 8.2, 7.2 |
| RF930307<3<BN0559-3-2-2 pl 3 | + | + | + | + | + | + | F | − | − | − | − | L | 15.4, 17.7 |
| RF930307<3<BN0559-3-2-2 pl 10 | + | + | + | + | + | + | F | − | − | − | − | L | 28.2, 28.5 |
| RF930307<3<BN0559-3-2-2 pl 7 | − | − | − | − | − | − | S | − | − | − | − | L | 26.9, 27.6 |
| RF930307<3<BN0559-3-2-2 pl 4 | − | − | − | − | − | − | S | − | − | − | − | L | 26.8, 26.7 |

+ presence of band
− absence of band
F fertile plant
S sterile plant
H high seed glucosinolates
L low seed glucosinolates

TABLE 7

| Probe name | Origin (see note 1) | Enzyme | Allele associated with Restorer | Approx .allele size (bp)* |
|---|---|---|---|---|
| pN213 | 1 | EcoRI | A | 23000 |
| WG3F7 | 3 | EcoRI | D | 7000 |
| TG1H12 | 3 | EcoRI | D | 3700 |
| OPC2 | 4 | | 1150 | 1150 |
| WG4D10 | 3 | EcoRI | J | 3400 |
| pO9 | 2 | EcoRI | O | 19000 |
| pN64 | 1 | EcoRI | D | 4300 |

TABLE 7-continued

| Probe name | Origin (see note 1) | Enzyme | Allele associated with Restorer | Approx. allele size (bp)* |
|---|---|---|---|---|
| pO119 | 2 | EcoRI | H | 6500 |
| pO120 | 2 | EcoRI | F | 4600 |
| WG6F3 | 3 | EcoRI | E | 13000 |

Note 1
1 Proprietary, genomic DNA, from *B napus*
2 Proprietary, genomic DNA, from *B oleracea*
3 T Osborn, U of Madison, WI
4 Oligonucleotide for RAPD analysis - Operon Inc.
*For certain probes other alleles of similar size may be segregating in some backgrounds. In such cases conditions for electrophoresis / digestion may need some modification.

Not only has the present invention been implemented in *Brassica napus* but it also had been implemented in other Brassica spp.

Rapa Work With This Gene

The low glucosinolate gene has been backcrossed into Zeneca *B. rapa* lines as follows:

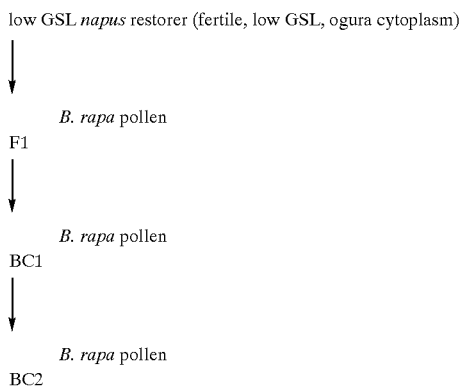

At the BC2 generation, both fertile and sterile plants have been obtained in an approximately 50:50 ratio. The plants are morphologically identical to the recurrent *B. rapa* parent. It is apparent that the restorer gene has been successfully introduced into the *Brassica rapa* species. Similar crossing techniques could be utilized to introduce this restorer gene into other Brassica species as well.

Conclusion

We have produced a clear improvement in the INRA ogura cms system of producing hybrid canolas. A strong linkage between the restorer gene introduced from *Raphanus sativus* and high glucosinolate genes from the same source was broken through an intensive crossing program. Based on the literature and all other publicly available information, there were no lines available to produce low glucosinolate, restored hybrids using the ogura cytoplasm until this work. It will now be possible to use this material (KH, and lines derived from it) as a source of fertility in all future canola-quality fertile Brassica hybrids using the ogura cytoplasm.

Furthermore, using the information given herein about where the probes used are located on the genome of ogura germplasm, it will be possible to use probes to test germplasm of this type to determine if it has the desired combination of restorer gene and low GLS. Accordingly, it is a further feature of our invention to provide ogura germplasm which gives a signal with probes binding in the restorer gene region of the genome, as shown in FIG. 1, but no signal with probes binding in the high GSL region of FIG. 1.

References

Chen, Z. Z., S. Snyder, Z. G. Fan and W. H. Loh 1994. Efficient production of doubled haploid plants through chromosome doubling of isolated microspores in *Brassica napus*. Plant Breeding 113:217–221.

Delourme, R., F. Eber and M. Renard. 1991. Radish cytoplasmic male sterility in rapeseed: breeding restorer lines with a good female fertility. Proc 8th Int Rapeseed Conf. Saskatoon, Canada. pp. 1506–1510.

Delourme, R., A. Bouchereau, N. Hubert, M. Renard and B. S. Landry. 1994. Identification of RAPD markers linked to a fertility restorer gene for the Ogura radish cytoplasmic male sterility of rapeseed (*Brassica napus* L.). Theor Appl Genet. 88:741–748.

Heyn, F. W. 1976. Transfer of restorer genes from Raphanus to cytoplasmic male-sterile *Brassica napus*. Cruciferae Newsletter. 1: 15–16.

Magrath, R., C. Herron, A. Giamoustaris and R. Mithen. 1993. The inheritance of aliphatic glucosinolates in *Brassica maps*. Plant Breeding 111: 55–72.

Ogura, H. 1968. Studies on the new male sterility in Japanese radish, with special reference on the utilization of this sterility towards the practical raising of hybrid seeds. Mem Fac Agric Kagoshima Univ. 6: 39–78.

Pelletier, G., C. Primard, F. Vedel, P. Chétrit, R. Rémy, P. Rousselle and M. Renard. 1983. Intergeneric cytoplasmic hybridization in Cruciferae by protoplast fusion. Mol Gen Genet. 191: 244–250.

Rakow, D., R. Gmelin and W. Thies. 1981. Enzymatische Darstellung und Eigenschaften einiger Desulfoglucosinolate. Z Naturforsch. 36: 16–22.

Mailer, R. J. and P. S. Cornish. 1987. Effects of water stress on glucosinolate and oil concentrations in the seed of rape (*Brassica napus* l) and turnip rape (*Brassica rapa* L. var. silvestris±Lam.Fr Briggs). Aust. J. Exp. Agric. 27:707–711.

Mollers, C., M. C. M. Iqbal and G. Robbelen. 1994. Efficient production of doubled haploid *Brassica napus* plants by colchicine treatment of microspores. Euphytica 75:95–104.

Rücker, B. and G. Rubbelen. 1994. Inheritance of total and individual glucosinolate contents in seeds of winter oilseed rape (*Brassica napus* L.). Plant Breeding. 113: 206–216.

Steele, R. G. D. and J. H. Torrie. 1980. Principles and Procedures of Statistics. McGraw-Hill Book Company.

We claim:

1. Brassica plant comprising a homozygous fertility restorer gene for Ogura cytoplasmic male sterility, wherein upon pollination the plant yields seeds having a total glucosinolate content of not more than 17 μmol e.g. per gram dry seed.

2. The seed of the Brassica plant of claim 1.

3. A Brassica plant according to claim 1 wherein said seed is canola quality.

4. The Brassica plant of claim 1 wherein the plant is *Brassica napus*.

5. A doubled haploid Brassica plant comprising a homozygous fertility restorer gene for Ogura cytoplasmic male sterility, wherein upon pollination the plant yields seeds having a total glucosinolate content of not more than 17 μmol e.g. per gram dry seed.

6. A seed of the plant of claim 5.

7. The seed of the plant of claim 5 wherein said plant is *Brassica napus*.

8. A Brassica plant of claim 1 comprising a part selected from the group comprising seeds, microspores, protoplasts, cells, ovules, pollen, vegetative parts, cotyledons, zygotes.

9. A part of a Brassica plant of claim 5 selected from the group comprising seeds, microspores, protoplasts, cells, ovules, pollen, vegetative parts, cotyledons, zygotes.

10. The Brassica plant of claim 1 wherein the plant is *Brassica rapa*.

11. The method of using a Brassica plant comprising the steps of: harvesting seed from a Brassica plant including a homozygous fertility restorer gene for Ogura cytoplasmic male sterility and include a total glucosinolate content of not more than 17 μmoles per gram dry seeds; and, planting said seed to produce progeny.

12. The method of claim 11 including the step of repeating a step of planting the harvested seed of the progeny plants that include a homozygous fertility restorer gene for Ogura cytoplasmic male sterility and include a total glucosinolate content of not more than 17 μmoles per gram dry seeds; and, harvesting seed therefrom.

13. Brassica plant and the seeds thereof comprising a homozygous fertility restorer gene for Ogura cytoplasmic male sterility, wherein upon pollination the plant yields seeds including at least one of the following total glucosinolate contents selected from the group of: not more than 14.0 μmoles per gram dry seed; not more than 10.5 μmoles per gram dry seed.

14. The seed of the Brassica plant of claim 5 wherein the plant and seed are negative for *Raphanus sativus* high glucosinolate production.

15. A doubled haploid Brassica plant comprising a homozygous fertility restorer gene for Ogura cytoplasmic male sterility, wherein upon pollination the plant yields seeds including at least one of the following total glucosinolate contents selected from the group of: not more than 14.0 μmoles per gram dry seed; not more than 10.5 μmoles per gram dry seed.

16. A seed of the plant of claim 15.

17. A Brassica plant of claim 13 comprising a part selected from the group comprising seeds, microspores, protoplasts, cells, ovules, pollen, vegetative parts, cotyledons, zygotes.

18. A part of a Brassica plant of claim 15 selected from the group comprising seeds, microspores, protoplasts, cells, ovules, pollen, vegetative parts, cotyledons, zygotes.

19. The method of using a Brassica plant comprising the steps of: harvesting seed from a Brassica plant including a homozygous fertility restorer gene for Ogura cytoplasmic male sterility and including at least one of the following total glucosinolate contents selected from the group of: not more than 14.0 μmoles per gram dry seed; not more than 10.5 μmoles per gram dry seed; and, planting said seed to produce progeny.

20. The method of claim 19 including the step of repeating the step of planting the harvested seed of the progeny plants that includes a homozygous fertility restorer gene for Ogura cytoplasmic male sterility and including at least one of the following total glucosinolate contents selected from the group of: not more than 14.0 μmoles per gram dry seed; not more than 10.5 μmoles per gram dry seed; and, harvesting seed therefrom.

21. A Brassica plant according to claim 13 comprising a homozygous fertility restorer gene for Ogura cytoplasmic male sterility and the selected total glucosinolate contents wherein the homozygous fertility restorer gene for Ogura cytoplasmic male sterility and the selected total glucosinolate contents are inherited and stable in the progeny of said plant.

\* \* \* \* \*